(12) United States Patent
Denzer et al.

(10) Patent No.: US 7,285,263 B2
(45) Date of Patent: Oct. 23, 2007

(54) COMPOSITIONS COMPRISING HYDROPHOBIC SILICONE OILS AND ALKYL ETHER CARBOXYLATES

(75) Inventors: Horst Denzer, Düsseldorf (DE); Hiroshi Abe, Barcelona (ES); Monika Pytlik, Duisburg (DE); Rosemarie Jansen, Emmerich/Elten (DE); Andrea Buhmann, Koblenz (DE)

(73) Assignee: KAO Chemicals Europe S.L., Barcelona (ES)

( * ) Notice: Subject to any disclaimer, the term of this patent is extended or adjusted under 35 U.S.C. 154(b) by 0 days.

(21) Appl. No.: 10/399,629

(22) PCT Filed: Oct. 26, 2001

(86) PCT No.: PCT/EP01/12435

§ 371 (c)(1),
(2), (4) Date: Aug. 14, 2003

(87) PCT Pub. No.: WO02/36081

PCT Pub. Date: May 10, 2002

(65) Prior Publication Data

US 2004/0047825 A1    Mar. 11, 2004

(30) Foreign Application Priority Data

Oct. 30, 2000   (DE)   ................ 100 53 727

(51) Int. Cl.
*A61K 7/075*   (2006.01)
(52) U.S. Cl. .................................. 424/70.12
(58) Field of Classification Search ................ 424/401, 424/70.12
See application file for complete search history.

(56) References Cited

U.S. PATENT DOCUMENTS

| | | | |
|---|---|---|---|
| 4,656,043 A * | 4/1987 | Hawkins et al. ............ 510/124 |
| 5,104,645 A | 4/1992 | Cardin et al. | |
| 5,180,584 A * | 1/1993 | Sebag et al. ................ 510/122 |
| 6,013,683 A | 1/2000 | Hill et al. | |
| 6,015,574 A | 1/2000 | Cannell et al. | |
| 6,071,975 A | 6/2000 | Halloran | |
| 6,410,493 B1 * | 6/2002 | Garnier ..................... 510/119 |
| 6,497,866 B2 * | 12/2002 | Irrgang et al. ........... 424/70.24 |
| 6,803,050 B2 * | 10/2004 | Denzer et al. ............. 424/401 |

FOREIGN PATENT DOCUMENTS

| | | |
|---|---|---|
| EP | 0 407 089 | 1/1991 |
| EP | 0 490 053 | 6/1992 |
| EP | 0 529 883 | 3/1993 |
| EP | 0 566 049 | 10/1993 |
| JP | 06293619 | 10/1994 |
| WO | WO 99/32079 | 7/1999 |

\* cited by examiner

*Primary Examiner*—Margaret G. Moore
(74) *Attorney, Agent, or Firm*—Gary M. Nath; Tanya E. Harkins; Ari G. Zytcer

(57) ABSTRACT

The invention relates to optically transparent compositions containing hydrophobic silicone oil and alkyl ether carboxylates that are useful e.g. as a hair treatment composition such as a shampoo. In particular, it provides an optically transparent composition comprising (a) a hydrophobic silicone oil; and (b) an alkyl ether carboxylate derived from alkanols having 6 to 22 carbon atoms; wherein the weight ratio of component (b) to component (a) is in the range of 1:1 to 20:1. The composition preferably also contains anionic surfactants as component (c), the total amount of the components (b) and (c) being preferably in the range of 10-25 wt.-% with respect to the total weight of the composition. The invention also provides a method for preparing the above composition.

12 Claims, No Drawings

COMPOSITIONS COMPRISING HYDROPHOBIC SILICONE OILS AND ALKYL ETHER CARBOXYLATES

The present invention relates to compositions containing hydrophobic silicone oil and alkyl ethercarboxylates which allow the preparation of optically transparent aqueous compositions that are useful e.g. as a hair treatment composition such as a shampoo.

Due to their very low surface tension, the spreadability of silicone oils on most surfaces such as ceramics, textiles, paper, skin, and hair, is excellent. In the field of personal care products, silicone oils are used because of their hair and skin smoothing properties, hair gloss enhancing properties and skin feel improving (non-oily, silky skin feel) properties. For many decades they are therefore ingredients in hairsprays, conditioners, colorants and sun protecting creams. In cosmetic rinse-off products like shampoos they appeared in the 1980ies and could obtain a considerable market share in the early 1990ies in the so-called "two-in-one" shampoos. These shampoos contain emulsified silicone oils. Silicone oil emulsions, however, show problems with respect to compatibility and stability, they show a strong foaminess reducing effect and furthermore they are generally not transparent. This is why hydrophilic silicone polyethers have been introduced into the market. But apart from their generally higher price, the conditioning effect of hydrophilic silicone polyethers on skin and hair is generally much lower than of the hydrophobic silicone oils.

In view of these problems, attempts have been made to provide aqueous compositions containing hydrophobic silicone oil, the silicone oil being in a solubilized or microemulsified state.

U.S. Pat. No. 6,013,683 describes a microemulsion containing 40 to 95 wt. % of a short chain linear siloxane and water, and 5 to 60 wt. % of non-ionic and/or cationic surfactants. However, the microemulsions disclosed in this patent are only transparent in a very narrow temperature range and easily become turbid when added to aqueous solutions.

EP 0 529 883 B1 discloses hair shampoo compositions containing sodium lauryl ether sulfate and cocoamido propyl betaine as surfactants and 1.0 wt.-% of silicone oil. The silicone oil was added as micro-emulsion prepared by an emulsion polymerization technique. Hence, EP 0 529 883 B1 does not disclose aqueous compositions containing silicone oil which may be easily prepared.

On the other hand, the inventors of the present invention previously published a method allowing the easy incorporation of silicone oil into shampoos (H. Denzer, R. Jansen, M. Reininghaus in "Parfümerie und Kosmetik"; 6/99, pages 18-20). However, the method only allowed for the incorporation of comparably low amounts of silicone oil such as 0.5 wt.-% when using wash-active matter within the range of 15-40 wt.-%. Higher amounts of hydrophobic silicone oil could only be solubilized by increasing the amount of wash-active matter which is, however, not acceptable for dermatological and environmental reasons as well as for price reasons.

In view of these drawbacks of the prior art, it is the object underlying the present invention to provide an easily preparable, optically transparent composition containing hydrophobic silicone oil being suitable, e.g. as hair shampoo.

This object of the present invention is solved by the provision of an optically transparent composition comprising (a) a hydrophobic silicone oil; and
(b) an alkyl ether carboxylate derived from alkanols having 6 to 22 carbon atoms; and
(c) ethoxylated products derived from polyhydric alcohols;
wherein the weight ratio of component (b) to component (a) is in the range of 1:1 to 20:1.

A hydrophobic silicone oil is generally a silicone oil which is soluble in paraffinic oil at 25° C. Hydrophobic silicone oils to be used according to the present invention include both volatile and non-volatile silicone oils.

Specific examples include a cyclic methyl siloxane having the formula $\{(CH_3)_2SiO\}_x$ in which x is 3-6, or short chain linear methyl siloxanes having the formula $((CH_3)_2SiO\{(CH_3)_2SiO\}_y Si(CH_3)_3$ in which y is 0-5.

Some suitable cyclic methyl siloxanes are hexamethylcyclotrisiloxanes ($D_3$), a solid with a boiling point of 134° C. and the formula $\{(Me_2)SiO\}_3$; octamethylcyclotetrasiloxane ($D_4$) with a boiling point of 176° C., a viscosity of 2.3 $mm^2/s$, and the formula $\{(Me_2)SiO\}_4$; decamethylcyclopentasiloxane ($D_5$) (cyclomethicone) with a boiling point of 210° C., a viscosity of 3.87 $mm^2/s$, and the formula $\{(Me_2)SiO\}_5$; and dodecamethylcyclohexasiloxane ($D_6$) with a boiling point of 245° C., a viscosity of 6.62 $mm^2/s$ and the formula $\{(Me_2)SiO\}_6$.

Some suitable short linear methyl siloxane are hexamethyldisiloxane (MM) with a boiling point of 100° C., viscosity of 0-65 $mm^2/s$, and formula $Me_3SiOMe_3$; octamethyltrisiloxane (MDM) with a boiling point of 152° C., viscosity of 1.04 $mm^2/s$, and formula $Me_3SiOMe_2SiOsiMe_3$; decamethyltetrasiloxane ($MD_2M$) with a boiling point of 194° C., viscosity of 1.53 $mm^2/s$, and formula $Me_3SiO(MeSiO)_2SiMe_3$; dodecamethylpentasiloxane ($MD_3M$) with a boiling point of 229° C., viscosity of 2.06 $mm_2/s$, and formula $Me_3SiO(Me_2SiO)_3SiMe_3$; tetradecamethylhexasiloxane ($MD_4M$) with a boiling point of 245° C., viscosity of 2.63 mm2/s, and formula $Me_3SiO(Me_2SiO)_4SiMe_3$; and hexadecamethylheptasiloxane ($MD_5M$) with a boiling point of 270° C., viscosity of 3.24 $mm^2/s$, and formula $Me_3SiO(Me_2SiO)_5SiMe_3$.

Furthermore, long chain linear siloxanes such as phenyltrimethicone, bis(phenylpropyl)dimethicone, dimethicone, and dimethiconol are also included.

The alkyl ether carboxylate derived from alkanols having 6 to 22 carbon atoms used as component (b) is preferably one satisfying the following formula (I):

Formula (I):

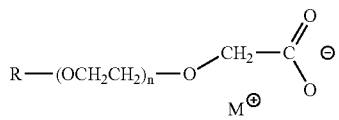

wherein R is an alkyl residue having 6 to 22 carbon atoms, n has a value in the range of 5 to 15, more preferably 7 to 10, and $M^+$ is an appropriate cation, preferably an alkaline metal cation such as sodium or potassium.

Particularly preferred are compounds of the above formula (I) wherein R is an alkyl residue having 8 to 16, more desirably 12 to 14 carbon atoms.

Alkyl ether carboxylates are preferably used as liquid concentrated aqueous solutions additionally containing nonionic surfactants such as ethoxylated products derived from polyhydric alcohols, such as glycerine, and/or additionally containing alcohol ethoxylates, preferably of the formula R(OCH$_2$CH$_2$)$_n$OH, wherein R and n have the same meaning as defined above for formula (I). Most preferred are Sodium Laureth-8 Carboxylate (marketed under the trade name 'AKYPO SOFT 70 NV by Kao Chemicals Europe), a mixture comprising Sodium Laureth-8 Carboxylate and Laureth-7 (marketed under the trade name 'AKYPO SOFT 70 BVC by Kao Chemicals Europe), and a mixture comprising 30 to 40 wt. % Sodium Laureth-11 Carboxylate, 20 to 30 wt. % Laureth-10 and 5 to 10 wt. % ethoxylated glycerine and carboxymethylated products thereof, the balance being water and sodium chloride (marketed under the trade name 'AKYPO SOFT 100 BVC by Kao Chemicals Europe). The preparation of corresponding mixtures is described in EP 0 580 263 B1.

The component (b) is used in a weight ratio of component (b) to silicone oil in the range of from 1:1 to 20:1, preferably 1:1 to 10:1, more preferably 2:1 to 8:1.

The composition of the present invention may be obtained simply by mixing component (a) with component (b) in the ratio indicated above. The components are mixed until the composition becomes optically transparent. According to the present invention, the term "optically transparent" means that the transmission of the composition in the visible region is at least 95%. The compositions of the present invention have preferably a transmission of more than 97%. The transmission is measured according to DIN 53995 using the Dr. Lange Liquid Tester LTM1 (supplied by Dr. Bruno Lange GmbH&Co. KG, Düsseldorf, Deutschland).

The composition of the present invention may optionally contain other surfactants as component (c), such as anionic surfactants. Preferred as anionic surfactant is sodium lauryl ether sulfate, particularly preferredis sodium lauryl ether sulfate having an average degree of ethoxylation of 1 to 3, preferably 1 to 2.5, most preferably 2 to 2.5. The anionic surfactant is desirablycontained in the composition in an amount of 3 to 15 wt. %, preferably 6 to 15 wt. %, with respect to the total weight of the composition.

If the composition of the present invention contains the component (c), the amount of alkyl ether carboxylate is preferably in the range of 2 to 10 wt. %, more preferably 5 to 8 wt. % with respect to the total weight of the composition. The amount of the hydrophobic silicone oil is preferably 1-3 wt.-%, more preferably 1.5 wt. % to 3 wt. % with respect to the total weight of the composition.

Further, the total amount of components (b) and (c) is preferably within the range of 10 to 25 wt. % with respect to the total weight of the composition, more preferably within the range of 12 to 20 wt. %. The total amount of wash active matter, that is, the total amounts of surfactants contained in the composition of the present invention is preferably less than 25 wt. %. That is, if the composition contains surfactants other than components (b) and (c), the total amount of these surfactants and components (b) and (c) does desirably not exceed 25 wt. %.

The viscosity of the composition of the present invention is preferably at least 1500 mPa·s, more preferably 2000-3000 mPa·s. The viscosity values indicated in the present invention are measured at 20° C. with a Brookfield viscometer LVT (supplied-by Brookfield Engineering Laboratories Inc. Stoughton, Mass., USA) in accordance with DIN 1341 (spindle 2 at 30 rpm for viscosities in the range of up to 1000 mPa s; spindle 3 at 12 rpm for viscosities in the range of 1000 to 7000 mPa s; spindle 4 at 12 rpm for viscosities in the range of more than 7000 mPa s).

The pH value of the composition of the present invention is preferably within the range of 5 to 8, more preferably 6 to 7.

The composition of the present invention may contain other surfactants such as non-ionic surfactants, cationic surfactants, and in particular amphoteric surfactants.

Amphoteric surfactant include ampholytes and betaines. Specific examples are alkyl amine oxides, alkyl betaines, alkyl sulphobetaines (sultaines), alkyl glycinates, alkyl carboxyglycinates, alkyl amphoacetates, alkyl amphopropionates, alklyamphoglycinates, alkyl amidopropyl betaines, alkyl amidopropyl- and hydroxysultaines. Particularly preferred amphoteric surfactants are alkyl sulphobetaines (sultaines), alklyamphoglycinates and alkyl amphoacetates. Even more preferred are alkyl hydroxysultaines, in particular lauryl hydroxysultaine. Amphoteric surfactants are preferably present in a weight ratio of alkyl ether carboxylate to amphoteric surfactant in the range of 1:3 to 3:1. The total amount of amphoteric surfactant is preferably between 4 and 8 wt. % with respect to the total amount of the composition.

The composition of the present invention may optionally contain fatty alcohols having 6 to 22 carbon atoms.

The composition of the present application may also contain deposition polymers. Suitable deposition polymers are any which enhance deposition of the silicone oil on the intented site, i.e. the hair or the skin. The deposition polymers disclosed in EP-B-529 883 are preferably used.

The composition of the present invention preferably also contains a vegetable oil. According to the present invention, the term vegetable oil means a mixture of saturated or unsaturated fatty acids having 6 to 22 carbon atoms, triglycerides thereof, esters thereof with alcohols having 6 to 22 carbon atoms, and the corresponding fatty alcohols having 6 to 22 carbon atoms. The vegetable oil may also be a terpinene-containing oil. Preferred examples of the vegetable oils to be used according to the present invention include evening prime rose oil, sesame oil and preferably jojoba oil, macadamia nut oil, tea tree oil, and avocado oil.

The vegetable oil is preferably contained in the composition of the present invention in a weight ratio of vegetable oil to silicone oil of 1:3 to 3:1, more preferably 1:1. The total amount of silicone oil and vegetable oil is preferably in the range of 2 to 6 wt. % with respect to the weight of the total composition.

If vegetable oil is present in the composition of the present invention, the hydrophobic silicone oil used is preferably a volatile hydrophobic silicone oil. Volatile hydrophobic silicone oils are silicone oils which evaporate from the hair surface at atmospheric pressure and room temperature.

The weight ratio of alkyl ether carboxylate to the total amount of silicone oil and vegetable oil is preferably in the range of 1:1 to 6:1, preferably 2:1 to 4:1.

The composition of the present invention may optionally contain further ingredients such as perfume, preservatives, thickeners, salts, and medically effective substances.

The method for preparing the composition of the present invention comprises the steps:
(a) mixing hydrophobic silicone oil with an alkyl ether carboxylate derived from alkanols having 6 to 22 carbon atoms in a weight ratio of alkyl ether carboxylate to silicone oil in the range of 1:1 to 20:1 at a temperatur of 20° C. or less; and
(b) stirring until an optically transparent composition is obtained.

Step (a) is generally carried out under gentle stirring such that incorporation of air into the mixture is minimized. For example, the mixture may simply be hand shaked or preferably stirred using a magnetic stirrer such as IKAMAG (supplied by Janke & Kunkel, Germany). When the mixture has a volume of less than 100 ml, the mixture is preferably stirred at less than 400 RPM, more preferably less than 200 RPM. Low stirring energies are not only advantageous in view of energy costs, but particularly in view of the fact that less air is incorporated into the solution. Air is generally difficult to remove afterwards from the aqueous solution once incorporated and may cause stability problems.

In the following step (b), the anionic surfactant such as sodium lauryl ether sulfate may be added before or while stirring until an optically transparent composition is obtained. The anionic surfactant is generally added in diluted form as aqueous solution in a concentration such that gelation is avoided in step (b). The concentration should preferably not exceed 30 wt.-%. Again, it is preferably only gently stirred in step (b).

In a further step (c), subsequent to step (b), the viscosity and the pH of the composition are preferably adjusted to the values indicated above, if necessary. The viscosity of the composition prior to step (c) depends on the component used. If the viscosity is found to be insufficient, e.g., below 1500 mPa·s, thickeners such as non-ionic surfactant-type thickeners such as Aminol N, Cocamide DEA and Cocamide MEA and derivatives thereof or polymeric thickeners such as PEG-150 distearate, PEG-120 methyl glucose dioleate, or PEG-160 sorbitan isostearate may be added. However, the amount of polymeric thickeners should preferably not exceed an amount of 1 wt.-% with respect to the total weight of the composition. Higher amounts of polymeric thickener may cause an unpleasant sticky feeling on skin during application.

The pH value may be adjusted to the range of 5 to 8 by adding pH adjusting agents known in the field. Examples for pH adjusting agents include citric acid and NaOH.

In the case that amphoteric surfactants are used as (co-)surfactants, they are preferably added after step (a) and prior to step (b). Further ingredients such as perfume and preservatives are usually added after step (c).

The compositions of the present invention show a number of beneficial properties in view of their high silicone content, and they may not only be used as personal care products such as shampoos, hair conditioners, hair dying agents, levelling agents, shower baths, liquid soaps and other cosmetic rinse-off products, but also in textile applications (softener) and plastic applications (plastic additives). The compositions are particularly useful as hair gloss shampoos, detangling shampoos, silky hair shampoos, fast drying shampoos, elderly people shampoos, colour care shampoos, special care shampoos.

EXAMPLES

In the example, all products used were obtained from Kao Chemicals Europe, unless indicated otherwise.

Example 1

Hair Gloss Shampoo

Shampoo Recipe (≈19% wash active matter; ≈22% total active matter)
(1) 25% EMAL 228D (28% a.m.) (INCI: Sodium Laureth Sulfate)
(2) 5% AKYPO SOFT 70 BVC (70% a.m.) (INCI: Sodium Laureth-8 Carboxylate (and) Laureth-7)
(3) 5% AKYPO SOFT 100 BVC (70% a.m.) (INCI: Sodium Laureth-11 Carboxylate (and) Laureth-10)
(4) 1% jojoba oil
(5) 1% Cyclomethicone ((IUPAC: Decamethylcyclopentasiloxane; supplied by Dow Corning)
(6) 5% AMINOL N (91% a.m.) (INCI: PEG-4 Rapeseedamide)
(7) 1% PEG-150 Distearate
(8) 3% sodium chloride q.s. at 100%: water, perfume, preservative, citric acid Shampoo Preparation:
(4) and (5) are stirred briefly (≈5 minutes) for intermixing
(2) and (3) are added and stirred until a homogeneous mixture is obtained (≈10 min)
(7) and water are heated to 50° C. until (7) dissolved (≈20 min), followed by addition of (1) and stirring for ≈5 minutes,
followed by addition of (6) (≈20 minutes stirring) and addition of preservative and perfume at a temperature below 30° C.
this mixtures (containing the components (7), (1) and (6) is added to the mixture containing the components (2) to (5) obtained above and stirring is continued until a homogeneous mixture is obtained (≈20 min
the pH—value is adjusted by adding citric acid (pH: 6-7) and viscosity (≈3000 mPas at 20° C.) is adjusted by addition of (8)

Example 2

29 wt. % AKYPO SOFT 70 BVC, 1.5 wt. % cyclomethicone and water (ad 100 wt. %) are mixed and stirred until a homogeneous and clear mixture is obtained (Ross Miles test: 170 mm after 30 seconds at 25° C.; 15°gh with 0.1% a.m.). 5 wt. % AMINOL N and 1 wt. % PEG-150 Distearate were then added, subsequently 4.5 wt. % NaCl to thicken the solution to a viscosity of 2000 mPas at 30° C.

The invention claimed is:
1. An optically transparent shampoo comprising:
(a) a hydrophobic silicone oil;
(b) an alkyl ether carboxylate derived from alkanols having 6 to 22 carbon atoms;
(c) sodium lauryl ether sulfate having an average degree of ethoxylated in the range of 1 to 3; and
(d) etholxyated glycerine,
wherein the weight ratio of component (b) to component (a) is in the range of 1:1 to 20:1, and
wherein component (c) is present in an amount of 6 to 15 weight percent.
2. The composition according to claim 1, wherein the total amount of components (b) and (c) is in the range of 10 to 25 wt. % with respect to the total weight of the composition.
3. The composition according to claim 1, having a pH value in the range of 5 to 8.
4. The composition according to claim 1, having a viscosity of at least 1500 mPa·s.
5. The composition according to claim 1, wherein the hydrophobic silicone oil is present in an amount of 1 to 3 wt. % with respect to the total weight of the composition.
6. The composition according to claim 1, wherein the hydrophobic silicone oil is a non-volatile silicone oil.
7. The composition according to claim 1, additionally containing an amphoteric surfactant.
8. The composition according to claim 7, wherein the amphoteric surfactant is lauryl hydroxysultaine.

9. The composition according to claim 7, wherein the amphoteric surfactant is present in an amount of 4 to 8 wt.-% with respect to the total weight of the composition.

10. Method for preparing a composition components (a) through (d).

11. An optically transparent composition comprising:
(a) a hydrophobic silicone oil;
(b) an alkyl ether carboxylate derived from alkanols having 6 to 22 carbon atoms;
(c) ethoxylated glycerine; and
(d) a vegetable oil,
wherein the weight ratio of component (b) to component (a) is in the range of 1:1 to 20:1.

12. The composition according to claim 11, wherein the hydrophobic silicone oil is a volatile silicone oil.

* * * * *

UNITED STATES PATENT AND TRADEMARK OFFICE
CERTIFICATE OF CORRECTION

| | | |
|---|---|---|
| PATENT NO. | : 7,285,263 B2 | |
| APPLICATION NO. | : 10/399629 | |
| DATED | : November 9, 2007 | |
| INVENTOR(S) | : Denzer et al. | |

It is certified that error appears in the above-identified patent and that said Letters Patent is hereby corrected as shown below:

Claim 1, Column 6, Line 47
Please delete "etholxyated" and replace with --ethoxylated--.

Claim 2, Column 6, Line 52
Please delete "composition" and replace with --shampoo--.

Claim 3, Column 6, Line 55
Please delete "composition" and replace with --shampoo--.

Claim 4, Column 6, Line 57
Please delete "composition" and replace with --shampoo--.

Claim 5, Column 6, Line 59
Please delete "composition" and replace with --shampoo--.

Claim 6, Column 6, Line 62
Please delete "composition" and replace with --shampoo--.

Claim 7, Column 6, Line 64
Please delete "composition" and replace with --shampoo--.

Claim 8, Column 6, Line 66
Please delete "composition" and replace with --shampoo--.

Claim 9, Column 7, Line 1
Please delete "composition" and replace with --shampoo--.

UNITED STATES PATENT AND TRADEMARK OFFICE
CERTIFICATE OF CORRECTION

PATENT NO. : 7,285,263 B2
APPLICATION NO. : 10/399629
DATED : November 9, 2007
INVENTOR(S) : Denzer et al.

It is certified that error appears in the above-identified patent and that said Letters Patent is hereby corrected as shown below:

Claim 10, Column 7, Lines 4-5
Please delete "a composition components (a) through (d)" and replace with
--a shampoo according to claim 1, comprising the steps of
(a) mixing a hydrophobic silicone oil and an alkyl ether carboxylate derived from alkanols having 6 to 22 carbon atoms with sodium lauryl ether sulfate having an average degree of ethoxylated in the range of 1 to 3 and ethoxylated glycerine, in a weight ratio of the alkyl ether carboxylate to the silicone oil in the range of 1:1 to 20:1; and
(b) stirring until an optically transparent shampoo composition is obtained.--

Signed and Sealed this

Fourth Day of March, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,285,263 B2 |
| APPLICATION NO. | : 10/399629 |
| DATED | : October 23, 2007 |
| INVENTOR(S) | : Denzer et al. |

It is certified that error appears in the above-identified patent and that said Letters Patent is hereby corrected as shown below:

Claim 1, Column 6, Line 47
Please delete "etholxyated" and replace with --ethoxylated--.

Claim 2, Column 6, Line 52
Please delete "composition" and replace with --shampoo--.

Claim 3, Column 6, Line 55
Please delete "composition" and replace with --shampoo--.

Claim 4, Column 6, Line 57
Please delete "composition" and replace with --shampoo--.

Claim 5, Column 6, Line 59
Please delete "composition" and replace with --shampoo--.

Claim 6, Column 6, Line 62
Please delete "composition" and replace with --shampoo--.

Claim 7, Column 6, Line 64
Please delete "composition" and replace with --shampoo--.

Claim 8, Column 6, Line 66
Please delete "composition" and replace with --shampoo--.

Claim 9, Column 7, Line 1
Please delete "composition" and replace with --shampoo--.

UNITED STATES PATENT AND TRADEMARK OFFICE
CERTIFICATE OF CORRECTION

PATENT NO. : 7,285,263 B2
APPLICATION NO. : 10/399629
DATED : October 23, 2007
INVENTOR(S) : Denzer et al.

It is certified that error appears in the above-identified patent and that said Letters Patent is hereby corrected as shown below:

Claim 10, Column 7, Lines 4-5
    Please delete "a composition components (a) through (d)" and replace with --a shampoo according to claim 1, comprising the steps of
    (a) mixing a hydrophobic silicone oil and an alkyl ether carboxylate derived from alkanols having 6 to 22 carbon atoms with sodium lauryl ether sulfate having an average degree of ethoxylated in the range of 1 to 3 and ethoxylated glycerine, in a weight ratio of the alkyl ether carboxylate to the silicone oil in the range of 1:1 to 20:1; and
    (b) stirring until an optically transparent shampoo composition is obtained.--

This certificate supersedes the Certificate of Correction issued March 4, 2008.

Signed and Sealed this

First Day of April, 2008

JON W. DUDAS
*Director of the United States Patent and Trademark Office*